United States Patent
Kaneumi et al.

(10) Patent No.: US 8,197,586 B2
(45) Date of Patent: Jun. 12, 2012

(54) POLYFLUOROALKYLPHOSPHONIC ACID, METHOD FOR PRODUCING THE SAME AND MOLD-RELEASING AGENT COMPRISING THE SAME AS ACTIVE INGREDIENT

(75) Inventors: Yoshiyama Kaneumi, Ibaraki (JP); Seiichiro Murata, Ibaraka (JP); Katsuyuki Sato, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 13/255,332

(22) PCT Filed: Mar. 9, 2010

(86) PCT No.: PCT/JP2010/053871
§ 371 (c)(1),
(2), (4) Date: Sep. 8, 2011

(87) PCT Pub. No.: WO2010/104065
PCT Pub. Date: Sep. 16, 2010

(65) Prior Publication Data
US 2011/0315050 A1 Dec. 29, 2011

(30) Foreign Application Priority Data

Mar. 13, 2009 (JP) ................................. 2009-060481
Mar. 13, 2009 (JP) ................................. 2009-060483

(51) Int. Cl.
*B29C 33/60* (2006.01)
*B29C 33/56* (2006.01)
*B28B 7/38* (2006.01)
*C07F 9/38* (2006.01)
(52) U.S. Cl. ......................... 106/38.22; 106/2; 106/38.2
(58) Field of Classification Search ............ 106/2, 38.2, 106/38.22; 562/25; 570/134
See application file for complete search history.

(56) References Cited

U.S. PATENT DOCUMENTS

| | | | | |
|---|---|---|---|---|
| 3,639,144 A | * | 2/1972 | Chance et al. | 427/303 |
| 3,719,448 A | * | 3/1973 | Chance et al. | 8/191 |
| 3,763,282 A | * | 10/1973 | Chance et al. | 558/161 |
| 3,910,886 A | * | 10/1975 | Chance et al. | 548/957 |
| 6,824,882 B2 | * | 11/2004 | Boardman et al. | 428/457 |

FOREIGN PATENT DOCUMENTS

| | | | |
|---|---|---|---|
| FR | 261650 A | * | 12/1988 |
| JP | 52-036588 | | 3/1977 |
| JP | 52-039587 | | 3/1977 |
| JP | 55-133490 | | 10/1980 |
| JP | 58-180597 | | 10/1983 |
| JP | 59-166596 | | 9/1984 |
| JP | 60-190309 | | 9/1985 |
| JP | 60-193615 | | 10/1985 |
| JP | 4506894 B1 | * | 7/2010 |
| WO | WO 03/102003 A1 | | 12/2003 |
| WO | WO 2007/105633 A1 | | 9/2007 |

OTHER PUBLICATIONS

International Search Report from corresponding PCT application No. PCT/JP2010-053871 dated Apr. 6, 2010, 3 pgs.
English translation of International Preliminary Report on Patentability from corresponding PCT application No. PCT/JP2010/053871 dated Oct. 27, 2011 (5 pgs).

* cited by examiner

*Primary Examiner* — Anthony J Green
(74) *Attorney, Agent, or Firm* — Brinks Hofer Gilson & Lione

(57) ABSTRACT

Disclosed is a polyfluoroalkylphosphonic acid represented by the general formula: $C_nF_{2n+1}(CH_2CF_2)_a(CF_2CF_2)_b(CH_2CH_2)_cP(O)(OH)_2$, wherein n is an integer of 1 to 6, a is an integer of 1 to 4, b is an integer of 1 to 3, and c is an integer of 1 to 3, or a salt thereof, which is a compound having a perfluoroalkyl group containing 6 or less carbon atoms, which is said to have low bioaccumulation potential, and being usable as an active ingredient of a mold-releasing agent. The polyfluoroalkylphosphonic acid is produced by hydrolyzing a polyfluoroalkylphosphonic acid diester represented by the general formula: $C_nF_{2n+1}(CH_2CF_2)_a(CF_2CF_2)_b(CH_2CH_2)_cP(O)(OR)_2$, wherein R is a $C_1$-$C_4$ alkyl group, n is an integer of 1 to 6, a is an integer of 1 to 4, b is an integer of 1 to 3, and c is an integer of 1 to 3.

9 Claims, No Drawings

POLYFLUOROALKYLPHOSPHONIC ACID, METHOD FOR PRODUCING THE SAME AND MOLD-RELEASING AGENT COMPRISING THE SAME AS ACTIVE INGREDIENT

RELATED APPLICATION

This application is a 35 U.S.C. §371 national phase filing of International Patent Application No. PCT/JP2010/053871, filed Mar. 9, 2010, through which and to which priority is claimed under 35 U.S.C. §119 to Japanese Patent Application Nos. 2009-060481, filed Mar. 13, 2009 and 2009-060483, filed Mar. 13, 2009.

TECHNICAL FIELD

The present invention relates to a polyfluoroalkylphosphonic acid, a method for producing the same, and a mold-releasing agent comprising the same as an active ingredient. More particularly, the present invention relates to a polyfluoroalkylphosphonic acid that can be used as, for example, an active ingredient of a mold-releasing agent, a method for producing the same, and such a mold-releasing agent.

BACKGROUND ART

Currently, molding plastic materials, rubber materials, and other polymeric materials using molds requires the use of mold-releasing agents, such as silicone oil, wax, talc, mica, and tetrafluoroethylene resin. Although silicone oil, wax, etc., have excellent mold releasability, such mold-releasing agents are transferred to molded products, thereby impairing the uniform coating properties, secondary processability, etc., of the molded products; in addition, the durability of mold release effect is not sufficient. As for tetrafluoroethylene resin, the durability of mold release effect and secondary processability are satisfactory; however, it is necessary to perform bake treatment to form a film on the molding surface of a mold in the mold-release process, and the same treatment is required for reprocessing. Consequently, many processes are required.

In order to solve these defects, mold-releasing agents comprising a $C_4$-$C_{20}$ polyfluoroalkyl group-containing phosphate ester as one of their active ingredients are proposed (see Patent Documents 1 to 3). These mold-releasing agents exhibit excellent mold releasability and have a longer mold release life than conventional mold-releasing agents; however, as the shape of molded products becomes more complicated in recent years, the mold-releasing agents are required to achieve much higher performance.

Meanwhile, polyfluoroalkylphosphonic acid esters are also widely used as starting materials for the synthesis of active ingredients of mold-releasing agents. The mold release performance of polyfluoroalkylphosphonic acids, when used as mold-releasing agents, is most likely developed in compounds having a perfluoroalkyl group containing 8 to 12 carbon atoms. In particular, phosphonate compounds having a perfluorooctyl group and represented by the formula:

are preferably used in this kind of application (see Patent Documents 4 to 7).

Incidentally, it is reported that phosphate or phosphonate compounds having a $C_8$-$C_{12}$ perfluoroalkyl group are biologically degraded in the environment and converted to compounds having relatively high bioaccumulation potential and environmental concentration, causing concerns for exposure during treatment processes, and release and diffusion from waste, treated base materials, etc., into the environment. Moreover, compounds having a perfluoroalkyl group containing 14 or more carbon atoms are very difficult to handle because of their physical and chemical properties, and hence, such compounds are rarely used in practice.

Furthermore, as for phosphate or phosphonate compounds having a perfluoroalkyl group containing 8 or more carbon atoms, generation and incorporation of perfluorooctanoic acids with high bioaccumulation potential is unavoidable during the production of these compounds. For these reasons, companies that produce such phosphate or phosphonate compounds have retreated from the production of the compounds or promoted the use of alternative compounds having a perfluoroalkyl group containing 6 or less carbon atoms.

However, compounds having a perfluoroalkyl group containing 6 or less carbon atoms cause a significant decrease in orientation on the surface of a treated substrate, and the melting point, glass transition point (Tg), etc., of the compounds are markedly lower than those of $C_8$ compounds. Accordingly, the compounds are highly influenced by their environmental conditions, such as temperature, humidity, stress, and contact with an organic solvent. Consequently, the desired performance cannot be sufficiently achieved, and durability and other properties are affected.

PRIOR ART DOCUMENT

Patent Document

Patent Document 1: JP-B-53-23270
Patent Document 2: JP-B-53-23271
Patent Document 3: JP-B-57-48035
Patent Document 4: JP-B-2-45572
Patent Document 5: JP-B-3-78244
Patent Document 6: JP-B-4-4923
Patent Document 7: JP-B-4-11366
Patent Document 8: WO 2007/105633 A1

OUTLINE OF THE INVENTION

Problem to be Solved by the Invention

An object of the present invention is to provide a polyfluoroalkylphosphonic acid that is a compound having a perfluoroalkyl group containing 6 or less carbon atoms, which is said to have low bioaccumulation potential, and having mold releasability equivalent to that of a mold-releasing agent comprising, as an active ingredient, a compound having a perfluoroalkyl group containing 8 or more carbon atoms, and that can be used as an active ingredient of a mold-releasing agent; and to provide a method for producing the same, as well as a mold-releasing agent comprising the same as an active ingredient.

Means for Solving the Problem

The present invention provides a polyfluoroalkylphosphonic acid represented by the general formula:

wherein n is an integer of 1 to 6, a is an integer of 1 to 4, b is an integer of 1 to 3, and c is an integer of 1 to 3, or a salt thereof.

The polyfluoroalkylphosphonic acid is produced by a hydrolysis reaction of a polyfluoroalkylphosphonic acid diester represented by the general formula:

$$C_nF_{2n+1}(CH_2CF_2)_a(CF_2CF_2)_b(CH_2CH_2)_cP(O)(OR)_2 \quad [II]$$

wherein R is a $C_1$-$C_4$ alkyl group, n is an integer of 1 to 6, a is an integer of 1 to 4, b is an integer of 1 to 3, and c is an integer of 1 to 3.

The polyfluoroalkylphosphonic acid or a salt thereof is used as an active ingredient of a mold-releasing agent to form a mold-releasing agent.

Effect of the Invention

When the polyfluoroalkylphosphonic acid of the present invention or a salt thereof is released into the environment, the —$CH_2CF_2$— bonding part of the molecule undergoes HF-elimination to form a double bond. The resulting compound is subjected to ozone decomposition etc., to have a structure that is easily decomposed into a compound with low environmental concentration and low bioaccumulation potential. Moreover, the polyfluoroalkylphosphonic acid or a salt thereof does not produce environmental burden substances, such as perfluoroalkyl carboxylic acids having 8 or more carbon atoms, in the production process thereof.

The polyfluoroalkylphosphonic acid or a salt thereof exhibits effective mold releasability, for example, when it is applied as an aqueous or organic solvent mold-releasing agent having a concentration of about 0.1 wt. % or less to an object to be subjected to a mold release treatment (e.g., a molding mold). This excellent effect is attributable to the extremely high solubility of the polyfluoroalkylphosphonic acid or a salt thereof in solvents. Mold-releasing agents whose mold releasability is much more excellent than that of conventional mold-releasing agents, which are prepared to have a solid matters content of 0.5 wt. %, can be formed at a solid matters content of about 0.1 wt. % or less.

Moreover, the excellent solubility of the polyfluoroalkylphosphonic acid or a salt thereof in solvents facilitates the formation of mold-releasing agent solutions with uniform concentration. Accordingly, precipitation problematically formed in conventional mold-releasing agents is not formed, and good storage stability is ensured.

Owing to the above-described various properties of the polyfluoroalkylphosphonic acid or a salt thereof, the mold-releasing agent of the present invention exhibits the following excellent effects:

(1) Film-forming properties are excellent, allowing the formation of uniform coating on molded products of a complicated shape.

(2) Film-forming properties for the mold surface and tightly adhesion to the mold surface due to ionic groups are excellent, significantly improving mold releasability and mold release life.

(3) Mold releasability and durability are excellent even after dilution to low concentration (e.g., about 0.1 wt. %), reducing mold contamination caused by the mold-releasing agent.

(4) Since the transmission of the mold-releasing agent to the molded product is low, the quality of the molded product after molding is less adversely affected, improving the dimensional accuracy of the molded product.

EMBODIMENTS FOR CARRYING OUT THE INVENTION

The polyfluoroalkylphosphonic acid [I] is produced by a hydrolysis reaction of a polyfluoroalkylphosphonic acid diester represented by the general formula:

$$C_nF_{2n+1}(CH_2CF_2)_a(CF_2CF_2)_b(CH_2CH_2)_cP(O)(OR)_2 \quad [II]$$

wherein R is a $C_1$-$C_4$ alkyl group, n is an integer of 1 to 6, a is an integer of 1 to 4, b is an integer of 1 to 3, and c is an integer of 1 to 3.

The polyfluoroalkylphosphonic acid diester [II], which is used as a starting material for this reaction, is obtained by the reaction of a polyfluoroalkyl iodide of the formula:

$$C_nF_{2n+1}(CH_2CF_2)_a(CF_2CF_2)_b(CH_2CH_2)_cI \quad [III]$$

with trialkyl phosphite $P(OR)_3$. The polyfluoroalkyl iodide [III] is a known compound, and is disclosed in Patent Document 8.

The polyfluoroalkyl iodide [III], which is used as a starting material for the synthesis of the polyfluoroalkylphosphonic acid diester [II], is produced by the addition reaction of a terminally iodized compound represented by the general formula:

$$C_nF_{2n+1}(CH_2CF_2)_a(CF_2CF_2)_bI \quad [IV]$$

with ethylene. The ethylene addition reaction is carried out in such a manner that the compound [IV] is subjected to an addition reaction with pressurized ethylene in the presence of a peroxide initiator. The number of addition is 1 to 3, preferably 1, although depending on the reaction conditions. Although the reaction temperature depends on the degradation temperature of the initiator used, the reaction is generally conducted at about 80 to 120° C.; when a peroxide initiator that decomposes at a low temperature is used, the reaction can be conducted at 80° C. or below.

As a peroxide initiator, tert-butyl peroxide, di(tert-butylcyclohexyl) peroxydicarbonate, dicetyl peroxydicarbonate, di-n-propyl peroxydicarbonate, diisopropyl peroxydicarbonate, di-sec-butyl peroxydicarbonate, or the like may be used at a ratio of about 1 to 5 mol % with respect to the amount of the compound [IV], in terms of the progressability and controllability of the reaction.

The terminally iodized compound [IV] is synthesized through a series of the following steps:

(1) A perfluoroalkyl iodide represented by the general formula:

$$C_nF_{2n+1}I \ (n: 1 \text{ to } 6)$$

is reacted with vinylidene fluoride in the presence of a peroxide initiator as described above in an amount of about 0.1 to 0.5 mol % based on the amount of the starting material compound to obtain a compound represented by the general formula:

$$C_nF_{2n+1}(CH_2CF_2)_aI \quad [V]$$

(2) The compound represented by the general formula [V] is reacted with tetrafluoroethylene in the presence of a peroxide initiator to thereby obtain a terminally iodized compound represented by the general formula [IV] described above. In the general formula [IV], b is an integer of 1 to 3, preferably 1 to 2. The organic peroxide initiator as mentioned above can be used as the peroxide initiator in this reaction in the same amount as in step (1).

Although the reaction temperature of the addition reaction of vinylidene fluoride and tetrafluoroethylene depends on the decomposition temperature of the initiator used, the use of a peroxide initiator that decomposes at a low temperature allows the reaction to occur at 80° C. or less under low-pressure conditions. The reaction is carried out in the following manner. The perfluoroalkyl iodide $C_nF_{2n+1}I$ or the compound [V] is charged in an autoclave, and the internal temperature is increased to about 10 to 60° C. For example, when the internal temperature reaches 50° C., a peroxide initiator dissolved in the perfluoroalkyl iodide $C_nF_{2n+1}I$ or the compound [V] is added thereto. When the internal temperature reaches 55° C., for example, vinylidene fluoride or tetrafluoroethylene is added in batches (as divided charges) while maintaining the pressure at about 0.1 to 0.6 MPa. After the desired amount of vinylidene fluoride or tetrafluoroethylene is added, aging is carried out, for example, at a temperature of about 55 to 80° C. for about one hour. The added amount of vinylidene fluoride or tetrafluoroethylene affects the number of vinylidene fluoride skeletons a or tetrafluoroethylene skeletons b added by the reaction. Generally, a mixture of various a values and b values is formed.

The fact that these reactions can be carried out at low temperatures indicates that not only energy usage can be reduced, but also corrosion due to hydrofluoric acid etc. in facilities can be prevented, thereby reducing the frequency of updating the facilities. Additionally, since more inexpensive materials can be used, capital investment costs can also be kept low, in addition to the decrease in update frequency.

Specific examples of the compound [IV] to which ethylene is added include the following compounds. These compounds are mixtures of oligomers having various a values and b values. Oligomers that have specific a and b values can be isolated by distilling the mixtures. Oligomers that do not have predetermined a and b values can be reused after isolation or as the mixtures in the reaction of increasing the number of oligomers with vinylidene fluoride or tetrafluoroethylene.

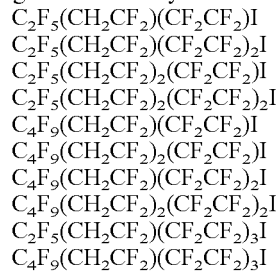

$C_2F_5(CH_2CF_2)(CF_2CF_2)I$
$C_2F_5(CH_2CF_2)(CF_2CF_2)_2I$
$C_2F_5(CH_2CF_2)_2(CF_2CF_2)I$
$C_2F_5(CH_2CF_2)_2(CF_2CF_2)_2I$
$C_4F_9(CH_2CF_2)(CF_2CF_2)I$
$C_4F_9(CH_2CF_2)_2(CF_2CF_2)I$
$C_4F_9(CH_2CF_2)(CF_2CF_2)_2I$
$C_4F_9(CH_2CF_2)_2(CF_2CF_2)_2I$
$C_2F_5(CH_2CF_2)(CF_2CF_2)_3I$
$C_4F_9(CH_2CF_2)(CF_2CF_2)_3I$

The polyfluoroalkyl iodide [III] prepared by the addition reaction of the compound [IV] as described above with ethylene can be reacted with trialkyl phosphite $P(OR)_3$ having an $C_1$-$C_4$ alkyl group, such as trimethyl phosphite, triethyl phosphite, tripropyl phosphite, or tributyl phosphite, to perform the RI-elimination reaction, thereby obtaining a polyfluoroalkylphosphonic acid diester [II], which is used as a starting material of the polyfluoroalkylphosphonic acid [I]. Without the addition reaction of the compound [IV] with ethylene, the RI-elimination reaction with trialkyl phosphite does not proceed.

The hydrolysis reaction of the polyfluoroalkylphosphonic acid diester [II] can be readily carried out by stirring at about 90 to 100° C. in the presence of an acidic catalyst, such as inorganic acid typified by concentrated hydrochloric acid. The resulting reaction mixture is filtered under reduced pressure, followed by water washing•filtration, acetone washing•filtration, and other methods, thereby obtaining the target compound polyfluoroalkylphosphonic acid [I] with a good yield of 90% or more.

The obtained polyfluoroalkylphosphonic acid can be used in the form of a salt after neutralization. The salt can be generally formed by titration with a salt-forming reactant, such as sodium hydroxide, ammonium hydroxide, zinc sulfate, zinc acetate, zinc oxide, triethylamine, morpholine, triethanolamine, or tris(2-hydroxyethyl), while identifying the equivalence point by the pH, to form an acidic mono-, di- or trivalent metal salt, amine salt, or ammonium salt. Examples of polyfluoroalkylphosphonic acid salts thus obtained include sodium, potassium, lithium, barium, magnesium, calcium, zinc, and other metal salts of polyfluoroalkylphosphonic acids; ammonium salts of polyfluoroalkylphosphonic acids; ammonium salts of polyfluoroalkylphosphonic acids substituted by alkyl or cycloalkyl groups, such as monoethyl, monoisopropyl, diethyl, dicyclohexyl, and triethyl; ammonium salts of polyfluoroalkylphosphonic acids substituted by hydroxyalkyl groups, such as monoethanol, diethanol, triethanol, and diisopropanol; and the like.

The preparation of a mold-releasing agent using the polyfluoroalkylphosphonic acid or a salt thereof can be carried out by dilution with water or organic solvent to form an aqueous solution, aqueous dispersion, or organic solvent solution having a solid matters content of about 0.01 to 30 wt. %, preferably about 0.05 to 3 wt. %. An example of usable organic solvents is at least one of alcohols, such as methanol, ethanol, n-propanol, and isopropanol; ketones, such as acetone, methyl ethyl ketone, and methyl isobutyl ketone; ethers, such as diethyl ether, diisopropyl ether, dioxane, and tetrahydrofuran; esters, such as ethyl acetate and butyl acetate; polyalcoholic derivatives, such as methyl cellosolve, ethyl cellosolve, methyl carbitol, and ethyl carbitol; halogenated hydrocarbons, such as carbon tetrachloride, methylene chloride, trichloroethylene, perchloroethylene, trichloroethane, trichlorofluoromethane, tetrachlorodifluoroethane, and trichlorotrifluoroethane; and the like. Preferably, a mixed solvent of isopropanol and ethanol is used. Here, the organic solvent can be used in combination with water.

The mold-releasing agent solution may contain, if necessary, amine-based neutralizers, such as triethylamine, triethanolamine, tris(2-hydroxyethyl)amine, and morpholine; various ionic and non-ionic surfactants for improving the wetting property of the mold-releasing agent; silicone oil, silicone varnish, etc., for further improving mold releasability and lubricity.

The mold-releasing agent solution can be applied to a mold by any common method such as dipping, spraying, brushing, aerosol spraying, or impregnated fabric coating. Moreover, examples of molding materials to be molded with a mold to which the mold-releasing agent is applied include polyurethane, polycarbonate, epoxy resin, phenol resin, polyimide resin, vinyl chloride resin, and other resins; natural rubber, chloroprene rubber, fluororubber, and other rubbers.

EXAMPLES

The following describes the present invention with reference to Examples.

Example 1

(1) In a 1-L capacity, four-necked flask equipped with a thermometer and a receiver for removing low-boiling substances, 500 g (0.78 mol) of a compound of the formula: $CF_3(CF_2)_3(CH_2CF_2)(CF_2CF_2)_2(CH_2CH_2)I$ (99GC %), and 181 g (1.56 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a slender tube. A slight amount of reaction solution was taken and subjected to gas chromatography analysis to confirm the remaining amount of triethyl phosphite. Thereafter, triethyl phosphite was further added in four batches in an amount of 91 g (0.78 mol) per batch, and the mixture was stirred for 18 hours in total.

After the reaction was completed, the reaction mixture was subjected to simple distillation under reduced pressure at an internal pressure of 0.2 kPa, an internal temperature of 160 to 170° C., and an overhead temperature of 150 to 155° C. The distillate fraction was washed with water, thereby obtaining 412 g (yield 78%) of a purified reaction product (96GC %).

The results of $^1$H-NMR and $^{19}$F-NMR confirmed that the resulting purified reaction product was a compound represented by the following formula:

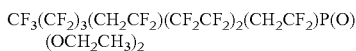

$^1$H-NMR (CD$_3$OD, TMS):
δ3.37 (C$\overline{H}_2$CF$_2$)
2.42 (C$\overline{H}_2$CH$_2$)
2.07 (C$\overline{H}_2$CH$_2$)
4.13 (CH$_2$C$\overline{H}_3$)
1.36 (C$\overline{H}_2$CH$_3$)
$^{19}$F-NMR (CD$_3$OD, C$_6$F$_6$):
ppm −80.2 (CF$_3$)
−124.6 (C$\overline{F}_3$CF$_2$CF$_2$CF$_2$)
−122.3 (CF$_3$C$\overline{F}_2$CF$_2$CF$_2$)
−110.0 (CF$_2$CH$_2$C$\overline{F}_2$)
−110.0 (C$\overline{F}_2$CH$_2$CF$_2$)
−120.0 (CH$_2$CF$_2$C$\overline{F}_2$CF$_2$)
−121.6 (CH$_2$CF$_2$C$\overline{F}_2$CF$_2$)
−122.1 (CF$_2$CF$_2$CH$_2$C$\overline{H}_2$)
−113.8 (C$\overline{F}_2$CF$_2$CH$_2$CH$_2$)

(2) In a 1-L capacity, four-necked flask equipped with a thermometer and a condenser, 300 g (0.44 mol) of the polyfluoroalkylphosphonic acid diester of the formula: CF$_3$(CF$_2$)$_3$(CH$_2$CF$_2$)(CF$_2$CF$_2$)$_2$(CH$_2$CH$_2$)P(O)(OCH$_2$CH$_3$)$_2$ (96GC %) obtained in step (1) above, and 300 g of about 35% concentrated hydrochloric acid were charged, and the mixture was stirred at 100° C. for 12 hours. After cooling, filtration under reduced pressure was performed to thereby collect 276 g of solid matters. The solid matters were washed with water and filtrated again, further followed by acetone washing and filtration, thereby obtaining 242 g (0.41 mol; yield 92%) of the target product.

The results of $^1$H-NMR and $^{19}$F-NMR confirmed that the resulting reaction product was the target compound (polyfluoroalkyiphosphonic acid) represented by the following formula:

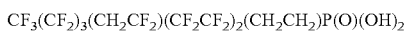

$^1$H-NMR (CD$_3$OD, TMS):
δ3.44 (C$\overline{H}_2$CF$_2$)
2.44 (C$\overline{H}_2$CH$_2$)
1.93 (C$\overline{H}_2$CH$_2$)
$^{19}$F-NMR (CD$_3$OD, C$_6$F$_6$):
ppm −80.2 (CF$_3$)
−124.6 (C$\overline{F}_3$CF$_2$CF$_2$CF$_2$)
−122.3 (CF$_3$C$\overline{F}_2$CF$_2$CF$_2$)
−110.0 (CF$_2$CH$_2$C$\overline{F}_2$)
−110.0 (C$\overline{F}_2$CH$_2$CF$_2$)
−120.0 (CH$_2$CF$_2$C$\overline{F}_2$CF$_2$)
−121.6 (CH$_2$CF$_2$C$\overline{F}_2$CF$_2$)
−122.3 (CF$_2$CF$_2$CH$_2$C$\overline{H}_2$)
−113.9 (C$\overline{F}_2$CF$_2$CH$_2$CH$_2$)

(3) The resulting polyfluoroalkylphosphonic acid (5 parts by weight) was added and mixed with 93.5 parts by weight of ion-exchanged water. To the mixture, 1.5 parts by weight of triethylamine was added to perform neutralization reaction, thereby preparing a mold-releasing agent A solution. The mold-releasing agent A solution was diluted 10 times with ion-exchanged water. Using the diluted mold-releasing agent solution, mold releasability and mold release life were evaluated in the following manner. The results were that the former was 7 N, and the latter was 12 times.

Mold releasability: 100 parts by weight of polyurethane prepolymer (Coronate C-4090, manufactured by Nippon Polyurethane Industry Co., Ltd.), which had been heated to 80° C., and 12.8 parts by weight of methylene-bis-o-chloroaniline curing agent (Iharacuamine MT, manufactured by Ihara Chemical Industry Co., Ltd.), which had been heat-melted, were mixed by stirring without forming air bubbles. The mixture was poured into an aluminum mold (diameter: 45 mm, depth: 50 mm) to which a mold-releasing agent had been applied by spraying, and which had been preheated to 80° C. After heat-curing at 120° C. for 1 hour, the cured molded product was taken out from the mold by pulling a hook, which had been previously stood in the center of the space of the mold for removing the molded product. The mold release load required to pull the hook was measured.

Mold release life: The same operations as the evaluation of the mold releasability were repeated to measure how many times with a one-time application of the mold-releasing agent allowed mold releasing at a mold release load of 5 kgf (49 N) or less.

Example 2

In Example 1 (3), a 20-fold dilution of the mold-releasing agent A solution with ion-exchanged water was used. The mold releasability was 10 N, and the mold release life was 10 times.

Example 3

In Example 1 (3), a 30-fold dilution of the mold-releasing agent A solution with ion-exchanged water was used. The mold releasability was 15 N, and the mold release life was 9 times.

Example 4

In Example 1 (3), a 40-fold dilution of the mold-releasing agent A solution with ion-exchanged water was used. The mold releasability was 19 N, and the mold release life was 7 times.

Example 5

In Example 1 (3), isopropyl alcohol and a mixed solvent of isooctane and isopropyl alcohol (weight ratio=90:10) were used respectively in the preparation and dilution of the mold-releasing agent A solution, in place of ion-exchanged waters. The mold releasability was 7 N, and the mold release life was 11 times.

Example 6

The polyfluoroalkylphosphonic acid (5 parts by weight) obtained in Example 1 (2) was added and mixed with 78.5 parts by weight of ion-exchanged water and 15 parts by weight of ethanol. To the mixture, 1.5 parts by weight of morpholine was added to perform neutralization reaction, thereby preparing a mold-releasing agent B solution. The mold-releasing agent B solution was diluted 20 times with ion-exchanged water. Using the diluted mold-releasing agent solution, mold releasability and mold release life were evaluated in the same manner as in Example 1 (3). The results were that the former was 9 N, and the latter was 10 times.

Example 7

The polyfluoroalkylphosphonic acid (5 parts by weight) obtained in Example 1 (2) was added and mixed with 78.5 parts by weight of ion-exchanged water, 12 parts by weight of ethanol, and 3 parts by weight of isopropanol. To the mixture, 1.5 parts by weight of triethylamine was added to perform neutralization reaction, thereby preparing a mold-releasing agent C solution. The mold-releasing agent C solution was diluted 20 times with ion-exchanged water. Using the diluted mold-releasing agent solution, mold releasability and mold release life were evaluated in the same manner as in Example 1 (3). The results were that the former was 8 N, and the latter was 10 times.

Example 8

(1) In a 1-L capacity, four-necked flask equipped with a thermometer and a receiver for removing low-boiling substances, 500 g (0.92 mol) of a compound of the formula: $CF_3(CF_2)_3(CH_2CF_2)(CF_2CF_2)(CH_2CH_2)I$ (99GC %) and 213 g (1.84 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a slender tube. A slight amount of reaction solution was taken and subjected to gas chromatography analysis to confirm the remaining amount of triethyl phosphite. Thereafter, triethyl phosphite was further added in four batches in an amount of 107 g (0.92 mol) per batch, and the mixture was stirred for 18 hours in total.

After the reaction was completed, the reaction mixture was subjected to simple distillation under reduced pressure at an internal pressure of 0.2 kPa, an internal temperature of 145 to 155° C., and an overhead temperature of 138 to 142° C. The distillate fraction was washed with water, thereby obtaining 407 g (yield 79%) of a purified reaction product (98GC %).

The results of $^1$H-NMR and $^{19}$F-NMR confirmed that the resulting purified reaction product was a compound represented by the following formula:

$$CF_3(CF_2)_3(CH_2CF_2)(CF_2CF_2)(CH_2CH_2)P(O)(OCH_2CH_3)_2$$

$^1$H-NMR ($CD_3OD$, TMS):
δ3.37 ($CH_2CF_2$)
2.43 ($\overline{CH}_2CH_2$)
2.07 ($C\overline{H}_2CH_2$)
4.13 ($CH_2\overline{CH}_3$)
1.36 ($C\overline{H}_2CH_3$)
$^{19}$F-NMR ($CD_3OD$, $C_6F_6$):
ppm −80.2 ($CF_3$)
−124.0 ($CF_3\overline{CF}_2CF_2CF_2$)
−122.3 ($CF_3C\overline{F}_2CF_2CF_2$)
−110.3 ($CFCH_2C\overline{F}_2$)
−109.8 ($C\overline{F}_2CH_2CF_2$)
−124.4 ($CH_2CF_2\overline{CF}_2CF_2$)
−113.1 ($CH_2CF_2C\overline{F}_2CF_2$)

(2) In a 1-L capacity, four-necked flask equipped with a thermometer and a condenser, 300 g (0.53 mol) of the polyfluoroalkylphosphonic acid diester of the formula: 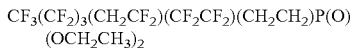$_3(CH_2CF_2)(CF_2CF_2)(CH_2CH_2)P(O)(OCH_2CH_3)_2$ (96GC %) obtained in step (1) above and 300 g of about 35% concentrated hydrochloric acid were charged, and the mixture was stirred at 100° C. for 12 hours. After cooling, filtration under reduced pressure was performed to thereby collect 287 g of solid matters. The solid matters were washed with water and filtrated again, further followed by acetone washing and filtration, thereby obtaining 240 g (0.49 mol; yield 93%) of the target product.

The results of $^1$H-NMR and $^{19}$F-NMR confirmed that the resulting reaction product was the target compound (polyfluoroalkylphosphonic acid) represented by the following formula:

$^1$H-NMR ($CD_3OD$, TMS):
δ3.44 ($CH_2CF_2$)
2.45 ($\overline{CH}_2CH_2$)
1.93 ($C\overline{H}_2CH_2$)
$^{19}$F-NMR ($CD_3OD$, $C_6F_6$):
ppm −80.2 ($CF_3$)
−124.0 ($CF_3\overline{CF}_2CF_2CF_2$)
−122.3 ($CF_3C\overline{F}_2CF_2CF_2$)
−110.3 ($CF_2CH_2C\overline{F}_2$)
−119.8 ($C\overline{F}_2CH_2CF_2$)
−124.6 ($CF_2CF_2C\overline{F}_2CH_2$)
−113.2 ($C\overline{F}_2CF_2CH_2CH_2$)

(3) Using 5 parts by weight of the resulting polyfluoroalkylphosphonic acid, the reaction was carried out in the same manner as in Example 7, thereby preparing a mold-releasing agent D solution. The mold-releasing agent D solution was diluted 20 times with ion-exchanged water. Using the diluted mold-releasing agent solution, mold releasability and mold release life were evaluated in the same manner as in Example 1 (3). The results were that the former was 14 N, and the latter was 9 times.

Example 9

(1) In a 1-L capacity, four-necked flask equipped with a thermometer and a receiver for removing low-boiling substances, 500 g (0.76 mol) of a compound of the formula: $CF_3(CF_2)(CH_2CF_2)(CF_2CF_2)_3(CH_2CH_2)I$ (97GC %) and 176 g (1.52 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a slender tube. A slight amount of reaction solution was taken and subjected to gas chromatography analysis to confirm the remaining amount of triethyl phosphite. Thereafter, triethyl phosphite was further added in four batches in an amount of 88 g (0.76 mol) per batch, and the mixture was stirred for 18 hours in total.

After the reaction was completed, the reaction mixture was subjected to simple distillation under reduced pressure at an internal pressure of 0.2 kPa, an internal temperature of 160 to 170° C., and an overhead temperature of 150 to 155° C. The distillate fraction was washed with water, thereby obtaining 395 g (yield 77%) of a purified reaction product (96GC %).

The results of $^1$H-NMR and $^{19}$F-NMR confirmed that the resulting purified reaction product was a compound represented by the following formula:

$^1$H-NMR ($CD_3OD$, TMS):
δ3.34 ($CH_2CF_2$)
2.42 ($\overline{CH}_2CH_2$)
2.07 ($C\overline{H}_2CH_2$)
4.13 ($CH_2\overline{CH}_3$)
1.36 ($C\overline{H}_2CH_3$)
$^{19}$F-NMR ($CD_3OD$, $C_6F_6$):
ppm −85.3 ($CF_3$)
−114.0 ($CF_3\overline{CF}_2CH_2CF_2$)
−110.2 ($CH_2C\overline{F}_2CF_2CF_2CF_2CF_2CF_2CF_2$)
−120.0 ($CH_2C\overline{F}_2CF_2CF_2CF_2CF_2CF_2CF_2$)

-119.5 (CH$_2$CF$_2$CF$_2$CF$_2$CF$_2$CF$_2$CF$_2$CF$_2$)
-120.3 (CH$_2$CF$_2$CF$_2$C$\overline{F_2}$CF$_2$CF$_2$CF$_2$CF$_2$)
-121.4 (CH$_2$CF$_2$CF$_2$CF$_2$C$\overline{F_2}$CF$_2$CF$_2$CF$_2$)
-122.0 (CH$_2$CF$_2$CF$_2$CF$_2$CF$_2$C$\overline{F_2}$CF$_2$CF$_2$)
-114.8 (CH$_2$CF$_2$CF$_2$CF$_2$CF$_2$CF$_2$C$\overline{F_2}$CF$_2$)

(2) In a 1-L capacity, four-necked flask equipped with a thermometer and a condenser, 300 g (0.44 mol) of the polyfluoroalkylphosphonic acid diester of the formula: CF$_3$(CF$_2$)(CH$_2$CF$_2$)(CF$_2$CF$_2$)$_3$(CH$_2$CH$_2$)P(O)(OCH$_2$CH$_3$)$_2$ (96GC %) obtained in step (1) above and 300 g of about 35% concentrated hydrochloric acid were charged, and the mixture was stirred at 100° C. for 12 hours. After cooling, filtration under reduced pressure was performed to thereby collect 276 g of solid matters. The solid matters were washed with water and filtrated again, further followed by acetone washing and filtration, thereby obtaining 237 g (0.40 mol; yield 90%) of the target product.

The results of $^1$H-NMR and $^{19}$F-NMR confirmed that the resulting reaction product was the target compound (polyfluoroalkylphosphonic acid) represented by the following formula:

CF$_3$(CF$_2$)(CH$_2$CF$_2$)(CF$_2$CF$_2$)$_3$(CH$_2$CH$_2$)P(O)(OH)$_2$ $^1$H-NMR (CD$_3$OD, TMS):
δ3.41 (CH$_2$CF$_2$)
2.44 (C$\overline{H_2}$CH$_2$)
1.93 (C$\overline{H_2}$CH$_2$)
$^{19}$F-NMR (CD$_3$OD, C$_6$F$_6$):
ppm -85.3 (CF$_3$CF$_2$)
-114.0 (CF$_3$$\overline{CF_2}$)
-110.2 (CH$_2$C$\overline{F_2}$CF$_2$CF$_2$CF$_2$CF$_2$CF$_2$CF$_2$)
-120.0 (CH$_2$C$\overline{F_2}$CF$_2$CF$_2$CF$_2$CF$_2$CF$_2$CF$_2$)
-119.5 (CH$_2$CF$_2$C$\overline{F_2}$CF$_2$CF$_2$CF$_2$CF$_2$CF$_2$)
-120.3 (CH$_2$CF$_2$CF$_2$C$\overline{F_2}$CF$_2$CF$_2$CF$_2$CF$_2$)
-121.4 (CH$_2$CF$_2$CF$_2$CF$_2$C$\overline{F_2}$CF$_2$CF$_2$CF$_2$)
-122.2 (CH$_2$CF$_2$CF$_2$CF$_2$CF$_2$C$\overline{F_2}$CF$_2$CF$_2$)
-114.7 (CH$_2$CF$_2$CF$_2$CF$_2$CF$_2$CF$_2$C$\overline{F_2}$CF$_2$)

(3) Using 5 parts by weight of the resulting polyfluoroalkylphosphonic acid, the reaction was carried out in the same manner as in Example 7, thereby preparing a mold-release agent E solution. The mold-release agent E solution was diluted 20 times with ion-exchange water. Using the diluted mold-release agent solution, mold releasability and mold release life were evaluated in the same manner as in Example 1 (3). The results were that the formed was 11 N, and the latter was 8 times.

Example 10

(1) In a 1-L capacity, four-necked flask equipped with a thermometer and a receiver for removing low-boiling substances, 500 g (0.90 mol) of a compound of the formula: CF$_3$(CF$_2$)(CH$_2$CF$_2$)(CF$_2$CF$_2$)$_2$(CH$_2$CH$_2$)I (97GC %) and 208 g (1.80 mol) of triethyl phosphite P(OC$_2$H$_5$)$_3$ were charged, and the mixture was stirred at 155° C. At this time, to remove the by-product, i.e., ethyl iodide, from the reaction system, nitrogen gas was bubbled into the reaction solution using a slender tube. A slight amount of reaction solution was taken and subjected to gas chromatography analysis to confirm the remaining amount of triethyl phosphite. Thereafter, triethyl phosphite was further added in four batches in an amount of 104 g (0.90 mol) per batch, and stirred for 18 hours in total.

After the reaction was completed, the reaction mixture was subjected to simple distillation under reduced pressure at an internal pressure of 0.2 kPa, an internal temperature of 145 to 155° C., and an overhead temperature of 138 to 141° C. The distillate fraction was washed with water, thereby obtaining 397 g (yield 78%) of a purified reaction product (97GC %).

The results of $^1$H-NMR and $^{19}$F-NMR confirmed that the resulting purified reaction product was a compound represented by the following formula:

CF$_3$(CF$_2$)(CH$_2$CF$_2$)(CF$_2$CF$_2$)$_2$(CH$_2$CH$_2$)P(O)(OCH$_2$CH$_3$)$_2$ $^1$H-NMR (CD$_3$OD, TMS):
δ3.34 (CH$_2$CF$_2$)
2.42 (C$\overline{H_2}$CH$_2$)
2.07 (C$\overline{H_2}$CH$_2$)
4.13 (CH$_2$C$\overline{H_3}$)
1.36 (C$\overline{H_2}$CH$_3$)
$^{19}$F-NMR (CD$_3$OD, C$_6$F$_6$):
ppm -85.3 (CF$_3$)
-114.0 (CF$_3$$\overline{CF_2}$CH$_2$CF$_2$)
-110.1 (CH$_2$C$\overline{F_2}$CF$_2$CF$_2$CF$_2$CF$_2$)
-120.1 (CH$_2$C$\overline{F_2}$CF$_2$CF$_2$CF$_2$CF$_2$)
-122.0 (CH$_2$CF$_2$C$\overline{F_2}$CF$_2$CF$_2$CF$_2$)
-122.4 (CH$_2$CF$_2$CF$_2$CF$_2$CF$_2$CF$_2$)
-113.9 (CH$_2$CF$_2$CF$_2$CF$_2$C$\overline{F_2}$CF$_2$)

(2) In a 1-L capacity, four-necked flask equipped with a thermometer and a condenser, 300 g (0.52 mol) of the polyfluoroalkylphosphonic acid diester of the formula: CF$_3$(CF$_2$)(CH$_2$CF$_2$)(CF$_2$CF$_2$)$_2$(CH$_2$CH$_2$)P(O)(OCH$_2$CH$_3$)$_2$ (95GC %) obtained in step (1) above and 300 g of about 35% concentrated hydrochloric acid were charged, and the mixture was stirred at 100° C. for 12 hours. After cooling, filtration under reduced pressure was performed to thereby collect 271 g of solid matters. The solid matters were washed with water and filtrated again, further followed by acetone washing and filtration, thereby obtaining 235 g (0.48 mol; yield 92%) of the target product.

The results of $^1$H-NMR and $^{19}$F-NMR confirmed that the resulting reaction product was the target compound (polyfluoroalkylphosphonic acid) represented by the following formula:

CF$_3$(CF$_2$)(CH$_2$CF$_2$)(CF$_2$CF$_2$)$_2$(CH$_2$CH$_2$)P(O)(OH)$_2$ $^1$H-NMR (CD$_3$OD, TMS):
δ3.41 (CH$_2$CF$_2$)
2.44 (C$\overline{H_2}$CH$_2$)
1.93 (C$\overline{H_2}$CH$_2$)
$^{19}$F-NMR (CD$_3$OD, C$_6$F$_6$):
ppm -85.3 (CF$_3$CF$_2$)
-114.0 (CF$_3$$\overline{CF_2}$)
-110.1 (CH$_2$C$\overline{F_2}$CF$_2$CF$_2$CF$_2$CF$_2$)
-120.1 (CH$_2$C$\overline{F_2}$CF$_2$CF$_2$CF$_2$CF$_2$)
-122.0 (CH$_2$CF$_2$C$\overline{F_2}$CF$_2$CF$_2$CF$_2$)
-122.6 (CH$_2$CF$_2$CF$_2$C$\overline{F_2}$CF$_2$CF$_2$)
-114.7 (CH$_2$CF$_2$CF$_2$CF$_2$C$\overline{F_2}$CF$_2$)

(3) Using 5 parts by weight of the resulting polyfluoroalkylphosphonic acid, the reaction was carried out in the same manner as in Example 7, thereby preparing a mold-release agent F solution. The mold-release agent F solution was diluted 20 times with ion-exchange water. Using the diluted mold-release agent solution, mold releasability and mold release life were evaluated in the same manner as in Example 1 (3). The results were that the formed was 12 N, and the latter was 8 times.

Example 11

(1) In a 1-L capacity, four-necked flask equipped with a thermometer and a receiver for removing low-boiling substances, 500 g (0.88 mol) of a compound of the formula:

$CF_3(CF_2)(CH_2CF_2)(CF_2CF_2)_2(CH_2CH_2)_2I$ (97GC %) and 204 g (1.76 mol) of triethyl phosphite $P(OC_2H_5)_3$, were charged, and the mixture was stirred at 155° C. At this time, to remove the by-product, i.e., ethyl iodide, from the reaction system, nitrogen gas was bubbled into the reaction solution using a slender tube. A slight amount of reaction solution was taken and subjected to gas chromatography analysis to confirm the remaining amount of triethyl phosphite. Thereafter, triethyl phosphite was further added in four batches in an amount of 104 g (0.90 mol) per batch, and the mixture was stirred for 18 hours in total.

After the reaction was completed, the reaction mixture was subjected to simple distillation under reduced pressure at an internal pressure of 0.2 kPa, an internal temperature of 145 to 155° C., and an overhead temperature of 140 to 142° C. The distillate fraction was washed with water, thereby obtaining 410 g (yield 79%) of a purified reaction product (97 GC %).

The results of $^1$H-NMR and $^{19}$F-NMR confirmed that the resulting purified reaction product was a compound represented by the following formula:

$$CF_3(CF_2)(CH_2CF_2)(CF_2CF_2)_2(CH_2CH_2)_2P(O)(OCH_2CH_3)_2$$

$^1$H-NMR (CD$_3$OD, TMS):
δ4.13 (C$\overline{H}_2$CH$_3$)
  3.34 (C$\overline{H}_2$CF$_2$)
  2.42 (C$\overline{H}_2$CH$_2$CH$_2$CH$_2$)
  2.07 (C$\overline{H}_2$CH$_2$CH$_2$CH$_2$)
  1.63 to 1.71 (CH$_2$C$\overline{H}_2$C$\overline{H}_2$CH$_2$)
  1.36 (CH$_2$C$\overline{H}_3$)
$^{19}$F-NMR (CD$_3$OD, C$_6$F$_6$):
ppm −85.3 (C$\overline{F}_3$CF$_2$)
  −110.1 (C$\overline{F}_2$CF$_2$CF$_2$CF$_2$CF$_2$)
  −113.9 (CH$_2$C$\overline{F}_2$CF$_2$CF$_2$CF$_2$CF$_2$)
  −114.0 (CF$_3$C$\overline{F}_2$)
  −120.1 (CH$_2$C$\overline{F}_2$CF$_2$CF$_2$CF$_2$CF$_2$)
  −122.0 (CH$_2$CF$_2$C$\overline{F}_2$CF$_2$CF$_2$CF$_2$)
  −122.4 (CH$_2$CF$_2$CF$_2$C$\overline{F}_2$CF$_2$CF$_2$)

(2) In a 1-L capacity, four-necked flask equipped with a thermometer and a condenser, 300 g (0.51 mol) of the polyfluoroalkylphosphonic acid diester of the formula: $CF_3(CF_2)(CH_2CF_2)(CF_2CF_2)_2(CH_2CH_2)_2P(O)(OCH_2CH_3)_2$ (97 GC %) obtained in step (1) above and 300 g of about 35% concentrated hydrochloric acid were charged, and the mixture was stirred at 100° C. for 12 hours. After cooling, filtration under reduced pressure was performed to thereby collect 269 g of solid matters. The solid matters were washed with water and filtrated again, further followed by acetone washing and filtration, thereby obtaining 240 g (0.46 mol; yield 90%) of the target product.

The results of $^1$H-NMR and $^{19}$F-NMR confirmed that the resulting reaction product was the target compound (polyfluoroalkylphosphonic acid) represented by the following formula:

$$CF_3(CF_2)(CH_2CF_2)(CF_2CF_2)_2(CH_2CH_2)_2P(O)(OH)_2$$

$^1$H-NMR (CD$_3$OD, TMS):
δ3.41 (C$\overline{H}_2$CF$_2$)
  2.44 (C$\overline{H}_2$CH$_2$CH$_2$CH$_2$)
  1.93 (C$\overline{H}_2$CH$_2$CH$_2$CH$_2$)
  1.66 to 1.72 (CH$_2$C$\overline{H}_2$C$\overline{H}_2$CH$_2$)
$^{19}$F-NMR (CD$_3$OD, C$_6$F$_6$):
ppm −85.3 (C$\overline{F}_3$CF$_2$)
  −110.1 (C$\overline{F}_2$CF$_2$CF$_2$CF$_2$CF$_2$)
  −114.0 (CF$_3$C$\overline{F}_2$)
  −114.7 (CH$_2$C$\overline{F}_2$CF$_2$CF$_2$CF$_2$CF$_2$)
  −120.1 (CH$_2$CF$_2$C$\overline{F}_2$CF$_2$CF$_2$C$\overline{F}_2$)
  −122.0 (CH$_2$CF$_2$CF$_2$CF$_2$CF$_2$CF$_2$)
  −122.6 (CH$_2$CF$_2$CF$_2$C$\overline{F}_2$CF$_2$CF$_2$)

Using 5 parts by weight of the resulting polyfluoroalkylphosphonic acid, the reaction was carried out in the same manner as in Example 7, thereby preparing a mold-release agent G solution. The mold-release agent G solution was diluted 20 times with ion-exchange water. Using the diluted mold-release agent solution, mold releasability and mold release life were evaluated in the same manner as in Example 1 (3). The results were that the formed was 12 N, and the latter was 8 times.

Example 12

(1) In a 1-L capacity, four-necked flask equipped with a thermometer and a receiver for removing low-boiling substances, 500 g (1.12 mol) of a compound of the formula: $CF_3(CF_2)(CH_2CF_2)(CF_2CF_2)(CH_2CH_2)I$ (98GC %) and 259 g (2.24 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a slender tube. A slight amount of reaction solution was taken and subjected to gas chromatography analysis to confirm the remaining amount of triethyl phosphite. Thereafter, triethyl phosphite was further added in four batches in an amount of 130 g (1.12 mol) per batch, and the mixture was stirred for 18 hours in total.

After the reaction was completed, the reaction mixture was subjected to simple distillation under reduced pressure at an internal pressure of 0.2 kPa, an internal temperature of 130 to 140° C., and an overhead temperature of 128 to 131° C. The distillate fraction was washed with water, thereby obtaining 405 g (yield 79%) of a purified reaction product (98 GC %).

The results of $^1$H-NMR and $^{19}$F-NMR confirmed that the resulting purified reaction product was a compound represented by the following formula:

$$CF_3(CF_2)(CH_2CF_2)(CF_2CF_2)(CH_2CH_2)P(O)(OCH_2CH_3)_2$$

$^1$H-NMR (CD$_3$OD, TMS):
δ3.34 (C$\overline{H}_2$CF$_2$)
  2.42 (C$\overline{H}_2$CH$_2$)
  2.07 (C$\overline{H}_2$CH$_2$)
  4.13 (CH$_2$C$\overline{H}_3$)
  1.36 (C$\overline{H}_2$CH$_3$)
$^{19}$F-NMR (CD$_3$OD, C$_6$F$_6$):
ppm −85.3 (C$\overline{F}_3$)
  −114.0 (CF$_3$C$\overline{F}_2$CH$_2$CF$_2$)
  −110.4 (C$\overline{H}_2$CF$_2$CF$_2$CF$_2$)
  −122.4 (CH$_2$C$\overline{F}_2$CF$_2$CF$_2$)
  −113.9 (CH$_2$CF$_2$C$\overline{F}_2$CF$_2$)

(2) In a 1-L capacity, four-necked flask equipped with a thermometer and a condenser, 300 g (0.63 mol) of the polyfluoroallcylphosphonic acid diester of the formula: $CF_3(CF_2)(CH_2CF_2)(CF_2CF_2)(CH_2CH_2)P(O)(OCH_2CH_3)_2$ (94 GC %) obtained in step (1) above and 300 g of about 35% concentrated hydrochloric acid were charged, and the mixture was stirred at 100° C. for 12 hours. After cooling, filtration under reduced pressure was performed to thereby collect 262 g of solid matters. The solid matters were washed with water and filtrated again, further followed by acetone washing and filtration, thereby obtaining 229 g (0.59 mol; yield 93%) of the target product.

The results of $^1$H-NMR and $^{19}$F-NMR confirmed that the resulting reaction product was the target compound (polyfluoroalkylphosphonic acid) represented by the following formula:

$$CF_3(CF_2)(CH_2CF_2)(CF_2CF_2)(CH_2CH_2)P(O)(OH)_2$$

$^1$H-NMR (CD$_3$OD, TMS):
δ3.41 (CH$_2$CF$_2$)
2.44 (C$\overline{H}_2$CH$_2$)
1.93 (CH$_2$C$\overline{H}_2$)
$^{19}$F-NMR (CD$_3$OD, C$_6$F$_6$):
ppm −85.3 (CF$_3$CF$_2$)
−114.0 (CF$_3$C$\overline{F}_2$)
−110.4 (CH$_2$C$\overline{F}_2$CF$_2$CF$_2$)
−122.6 (CH$_2$CF$_2$C$\overline{F}_2$CF$_2$)
−114.0 (CH$_2$CF$_2$CF$_2$C$\overline{F}_2$)

Using 5 parts by weight of the resulting polyfluoroalkylphosphonic acid, the reaction was carried out in the same manner as in Example 7, thereby preparing a mold-release agent H solution. The mold-release agent H solution was diluted 20 times with ion-exchange water. Using the diluted mold-release agent solution, mold releasability and mold release life were evaluated in the same manner as in Example 1 (3). The results were that the formed was 14 N, and the latter was 7 times.

Using 5 parts by weight of a polyfluoroalkylphosphonic acid represented by the formula: CF$_3$(CF$_2$)$_7$(CH$_2$CH$_2$)P(O)(OH)$_2$ and having a perfluoroalkyl group containing 8 or more carbon atoms, the reaction was carried out in the same manner as in Example 7, thereby preparing a mold-release agent I solution. The mold-release agent I solution was diluted 20 times with ion-exchange water. Using the diluted mold-release agent solution, mold releasability and mold release life were evaluated in the same manner as in Example 1 (3). The results were that the formed was 13 N, and the latter was 5 times.

Comparative Example

In Example 1, the mold releasability and mold release life were evaluated without using a mold-releasing agent. The results were that the former was not measurable because the molded product was not removed from the mold, and consequently the mold release life was 0 times.

The invention claimed is:

1. A polyfluoroalkylphosphonic acid represented by the general formula:

$$C_nF_{2n+1}(CH_2CF_2)_a(CF_2CF_2)_b(CH_2CH_2)_cP(O)(OH)_2 \quad [I]$$

wherein n is an integer of 1 to 6, a is an integer of 1 to 4, b is an integer of 1 to 3, and c is an integer of 1 to 3, or a salt thereof.

2. The polyfluoroalkylphosphonic acid salt according to claim 1, wherein the salt of polyfluoroalkylphosphonic acid is an acidic mono-, di- or trivalent metal salt, amine salt, or ammonium salt.

3. A method for producing the polyfluoroalkylphosphonic acid of claim 1, the method comprising hydrolyzing a polyfluoroalkylphosphonic acid diester represented by the general formula:

$$C_nF_{2n+1}(CH_2CF_2)_a(CF_2CF_2)_b(CH_2CH_2)_cP(O)(OR)_2 \quad [II]$$

wherein R is a C$_1$-C$_4$ alkyl group, n is an integer of 1 to 6, a is an integer of 1 to 4, b is an integer of 1 to 3, and c is an integer of 1 to 3, or a salt thereof.

4. A mold-releasing agent comprising, as an active ingredient, a polyfluoroalkylphosphonic acid represented by the general formula:

$$C_nF_{2n+1}(CH_2CF_2)_a(CF_2CF_2)_b(CH_2CH_2)_cP(O)(OH)_2 \quad [I]$$

wherein n is an integer of 1 to 6, a is an integer of 1 to 4, b is an integer of 1 to 3, and c is an integer of 1 to 3, or a salt thereof.

5. The mold-releasing agent according to claim 4, which is used as an aqueous solution.

6. The mold-releasing agent according to claim 4, which is used as an aqueous dispersion.

7. The mold-releasing agent according to claim 4, which is used as an organic solvent solution.

8. The mold-releasing agent according to claim 4, wherein the polyfluoroalkylphosphonic acid or a salt thereof has solid matter of about 0.01 to 30 wt. %.

9. The mold-releasing agent according to clam 4, which is applied to a forming mold for use.

* * * * *